(12) United States Patent
Lin et al.

(10) Patent No.: US 7,270,636 B2
(45) Date of Patent: Sep. 18, 2007

(54) APPARATUS AND METHOD FOR PULSE DETECTION

(75) Inventors: Kang-Ping Lin, Jhongli (TW); Hong-Dun Lin, Taipei (TW); Bor-Iuan Jan, Pingtung (TW); Mei-Feng Chen, Guantian Township (TW)

(73) Assignee: DailyCare BioMedical Inc., Chung-Li (TW)

( * ) Notice: Subject to any disclaimer, the term of this patent is extended or adjusted under 35 U.S.C. 154(b) by 0 days.

(21) Appl. No.: 11/163,881

(22) Filed: Nov. 2, 2005

(65) Prior Publication Data
US 2006/0229517 A1  Oct. 12, 2006

(30) Foreign Application Priority Data
Apr. 11, 2005 (TW) ............................... 94111427 A

(51) Int. Cl.
*A61B 5/02* (2006.01)
(52) U.S. Cl. ...................... 600/490; 600/494; 600/496
(58) Field of Classification Search ............... None
See application file for complete search history.

(56) References Cited

U.S. PATENT DOCUMENTS

| 6,589,186 B2 * | 7/2003 | Nishibayashi ............... 600/494 |
| 2002/0077557 A1 * | 6/2002 | Cheng ........................ 600/490 |

\* cited by examiner

*Primary Examiner*—Robert L. Nasser
(74) *Attorney, Agent, or Firm*—Alan Kamrath; Kamrath & Associates PA

(57) ABSTRACT

An apparatus and method for pulse detection based on blood pressure measuring stage is disclosed. Both monitoring of blood pressure and blood vessel pulse are integrated and applied to an apparatus. With the components of the blood pressure monitor, such as an inflatable cuff an air pump and a variable flow valve, with a unique sequential pressure control of reduction and regulation of pressure, not only can blood pressure parameters but also pulse signals under various pressures be measured to provide a complete analysis of blood artery/vessel conditions.

16 Claims, 6 Drawing Sheets

APPARATUS AND METHOD FOR PULSE DETECTION

BACKGROUND OF THE INVENTION

1. Field of the Invention

The present invention relates to an apparatus and a method for pulse detection and, more particularly, to an apparatus and a method based on the blood pressure measuring stage to provide blood pressure parameters and acquire pulse signals further using unique sequential reduction and regulation of pressure.

2. Description of Prior Art

With the increase in cardiovascular disease, often due to sedentary lifestyle and over work, the frequency of hypertension, arteriosclerosis, and myocardial infarction become a serious concern. Blood pressure control is an important means of preventing and treating such cardiovascular system problems.

In medical treatment, blood pressure control is very important to prevent and take care of cardiovascular disease. World Health Organization's (WHO) standards for maximum healthy blood pressure define systolic pressure below 139 mmHg, and diastolic pressure below 89 mmHg, with the number being adjusted in accordance with correction for age and gender. Furthermore, to deal with and prevent cardiovascular diseases, the WHO suggests systolic pressure be set at 120 mmHg and diastolic pressure at 80 mmHg, standards which represent the need for special caution.

Many kinds of electronic dynamometers exist on the market, such as arm type, wrist type, and others. Such devices are convenient for self-monitoring. However, devices providing only blood pressure monitoring fail to take into account health of blood vessels, directly affecting the cardiovascular system. Monitoring of blood vessels is not, however, commonly available to average patients.

Although diagnostic apparatus for blood vessel condition in a non-invasive fashion based on pressure sensor has been clinically developed, the apparatus is used for calculating Stiffness Index (SI) and Reflection Index (RI) by detecting a pulse so as to estimate the attrition on blood vessels. However, the devices are not only expensive, but are also of a size limited to clinical use. If a patient wants to know the condition of their own blood vessels, they still need to go to the hospital for a professional level check. The present invention provides not only blood pressure measuring, but also detection of pulse signals at different pressures, using unique sequential reduction and regulation of pressure. The method measures both SI and RI, but also three different levels of Chinese Medical pulse diagnosis.

SUMMARY OF THE INVENTION

According to the present invention, an apparatus for pulse detection based on a blood pressure monitor detects blood pressure and pulse signals through pressure regulation, providing blood vessel analysis.

The present invention further provides a method of pulse detection. The method is based on modern sphygmomanometry and utilizes pressure control to detect the pulse and estimates the condition of blood vessels.

The present invention still further provides an apparatus for diagnostic analysis of blood vessels to detect blood pressure parameters and pulse signals. Pressure, pulse, and elasticity of blood vessels are acquired to diagnose the cardiovascular system.

Further, the present invention provides an apparatus for pulse detection combined with Chinese Medical pulse diagnosis. Controlling pressure of drift, middle and deep levels of Chinese Medical pulse diagnosis theory, waveforms under various pressures are detected and further provided for diagnosis.

To achieve the above aims, the present invention detects blood pressure, combined with detection of pulse of a blood vessel. The apparatus includes an inflatable cuff around a subject's arm, connected to an air pump and a pressure sensor. Utilizing inflation via the air pump, the pressure sensor detects a signal of pressure variation in the inflatable cuff during inflation.

Signal of pressure variation is analyzed through a signal processor module to acquire a pressure signal and a resonance signal, both of which are delivered to a CPU for processing to acquire a plurality of blood pressure parameters, and this is followed by application of a pressure relief valve connected to the inflatable cuff. The inflatable cuff with a unique sequential pressure control of reduction and regulation of pressure is applied according to at least one of the blood pressure parameters or at least one predetermined pressure. The inflatable cuff is sequentially maintained at the blood pressure parameter or the predetermined pressure for a predetermined time. The pressure sensor detects a signal through the unique sequential pressure control of reduction and regulation of pressure. After analysis of the signal by the signal processor module and transmission of the signal to the CPU, the measured pulse and parameters of blood pressure under various pressures are acquired.

The objects, features and effects of the present invention will be more readily understood from the following detailed description of the preferred embodiments with the appended drawings.

DETAILED DESCRIPTION OF THE INVENTION

In the following detailed description of the preferred embodiments, it is understood that other embodiments may be utilized and structural changes may be made without departing from the scope of the invention. The present invention will be further described in conjunction with accompanying drawings, which illustrate preferred (best mode) embodiments. A method and apparatus for pulse detection based on blood pressure measuring stage is disclosed according to the present invention. The present invention applies blood pressure detection as applied in conventional sphygmomanometers, combined with the technique for pulse detection. Thus, the present invention not only monitors blood pressure as the conventional sphygmomanometer, but also acquires various pulse signals at various pressures using a pressure control method. The present invention provides not only analysis of a blood vessel but is also applicable in Chinese Medical pulse diagnosis.

Figures 1A, 1B:
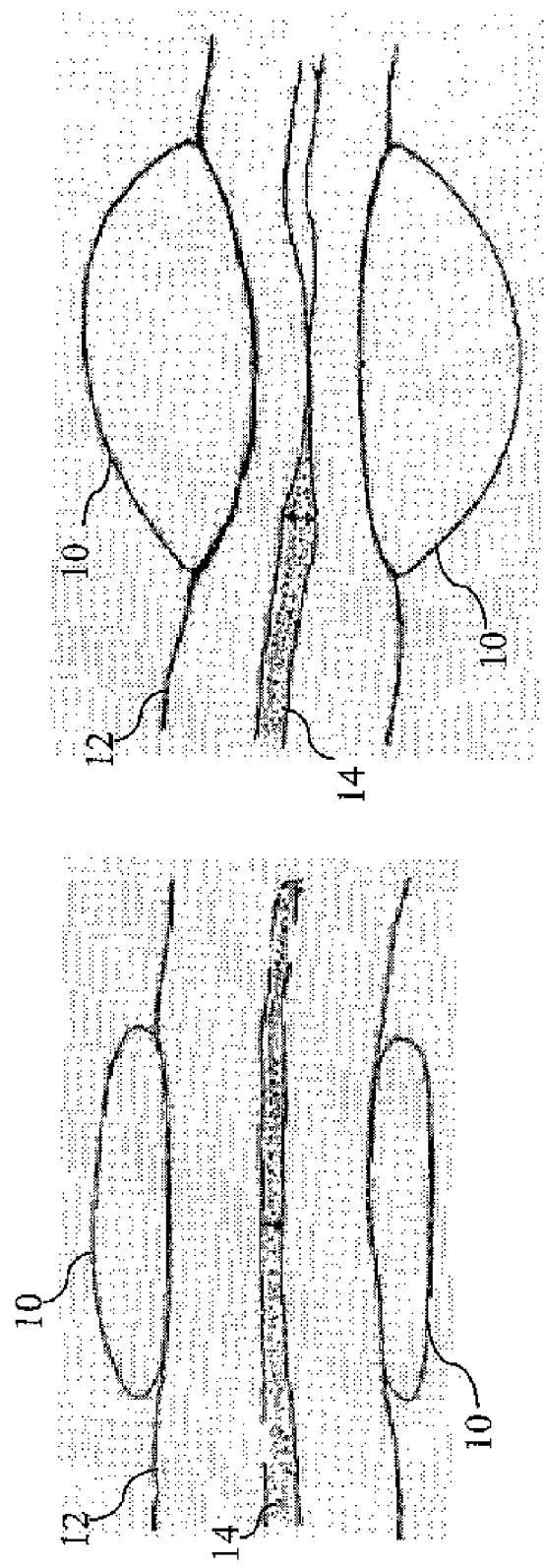
FIG. 1A is a schematic diagram showing deployment of an inflatable cuff of the present invention.
FIG. 1B is a schematic diagram showing the inflatable cuff applying pressure.

Principles of sphygmomanometric measurement are described as follows for better understanding of the present invention. The sphymomanometer in the market conventionally uses an auscultatory method, such as a mercury sphygmomanometer, and resonance method, as applied in most electric sphygmomanometry. Both applications use an inflatable cuff to restrict the blood flow in the vessel, then measuring systolic pressure, diastolic pressure, and mean arterial pressure through pressure in the inflatable cuff. As shown in FIG. 1A, a sphygmomanometer includes an inflatable cuff 10 wound around the subject's arm 12, whereby pressure is raised by inflation via a pump exceeding systolic pressure. An arterial blood vessel 14 is, thus, compressed and blood flow blocked, as shown in FIG. 1B. As the pressure of the inflatable cuff 10 is gradually decreased, blood flow resumes through the new un-blocked blood vessel 14. A slight pulse of the wall of the blood vessel 14 is produced and the variation of blood flow therein due to systolic action produces pressure oscillations in the inflatable cuff 10. Signals from pressure variations within the inflatable cuff 10 and the oscillating signals of pressure reflected by the blood vessel 14 are then detected by the pressure sensor.

Figure 2:
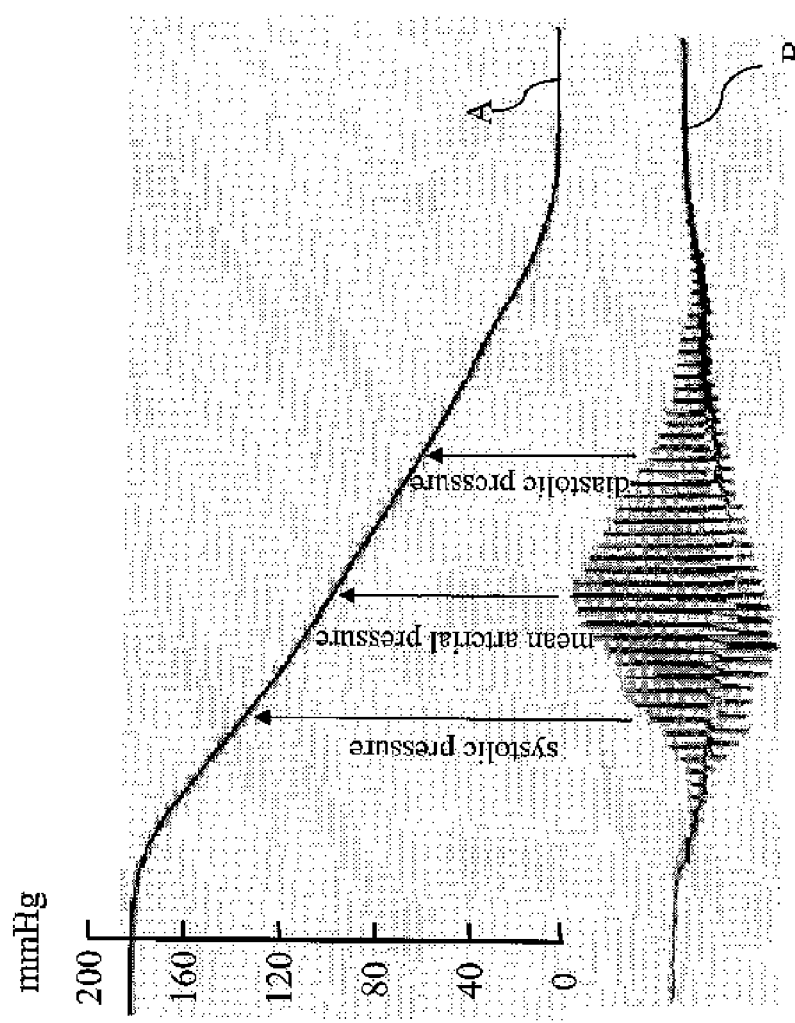
FIG. 2 is a schematic diagram showing the calculation of blood parameters.

Referring to FIG. 2, the two signals mentioned are separated after processing, and curve A of a signal of pressure variation in the inflatable cuff 10 and curve B of oscillating signals of pressure reflected by blood vessel 14 are acquired. When the maximum value of the oscillating amplitude is reached, the pressure is set as mean arterial pressure (MAP), and the systolic pressure and the diastolic pressure are estimated accordingly. For example, if the pressure of the inflatable cuff 10 goes from high to low, the systolic pressure occurs at half of the maximum amplitude before the maximum amplitude. The diastolic pressure occurs at 0.78 multiple value of the maximum amplitude after the maximum amplitude. The value for estimating is adjusted and corrected in accordance with different elements and clinical results.

Figure 3:
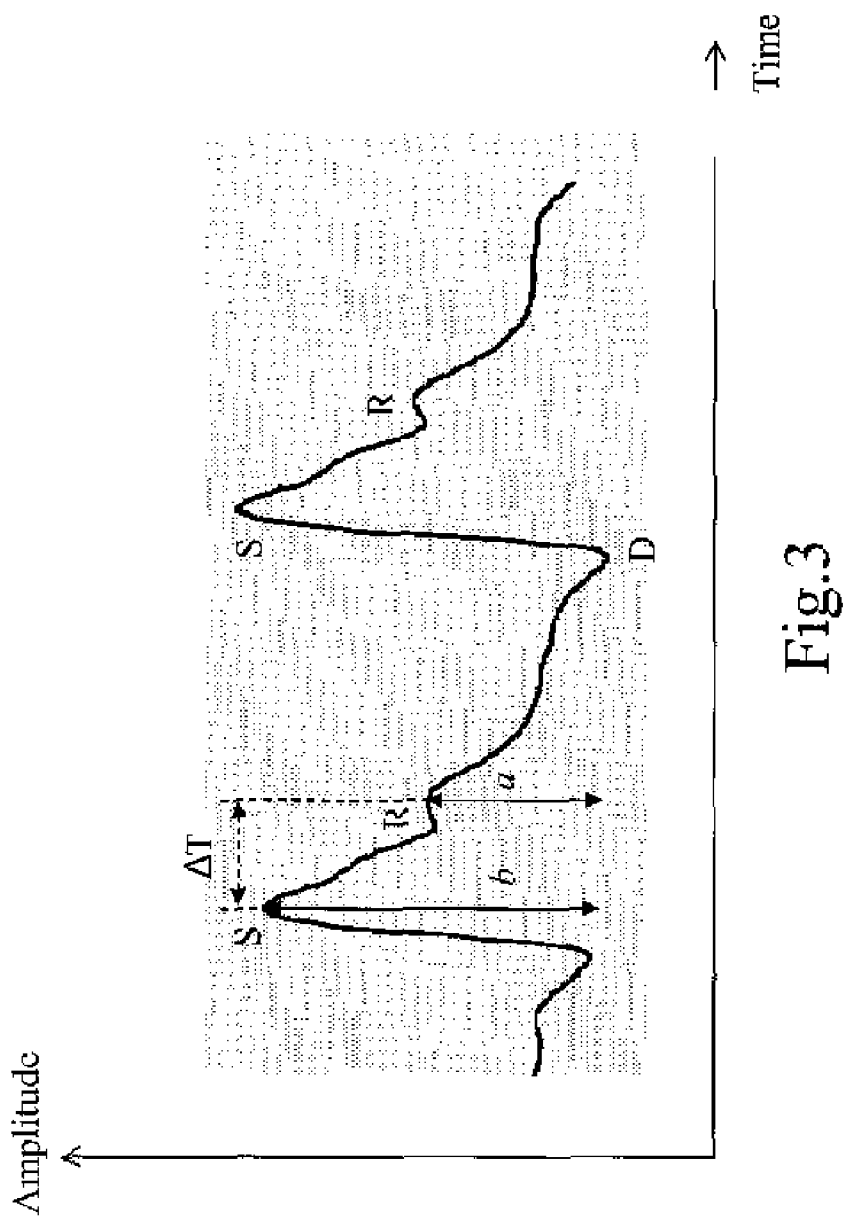
FIG. 3 is a schematic diagram showing pulse wave of the blood vessel.

Optical and pressure methods are also used to measure pulse. The optical method utilizes the difference in the concentration of oxygen in the blood due to the result of heart contraction and heart diastole to measure the absorption and reflection quantities in the blood. The pressure method is similar as mentioned, wherein, when a blood vessel is compressed, the blood flow as the result of heart contraction and heart diastole will impact to the vessel wall differently. Pulse is thus obtained. Using a pulse waveform of a subject's finger for example, as shown in FIG. 3, the first peak S occurs by heart contraction, and peak D by heart diastole. The second peak R is a reflected signal transmitted along the aorta. Delay time between the first and second peaks S and R depends on the transmit time of the pulse transmitting along a subclavian artery to a lower body of the subject and reflecting back to the subclavian artery. Assuming the pulse transmit distance is directly proportional to a subject's height, and assuming pulse transmission time from the aorta to large arteries is related to resilience of the blood vessel 14, large artery stiffness can be estimated using the following formula:

$$SI = \frac{\text{Subject height}}{\Delta T} \text{ in ms} \qquad (1)$$

SI □Stiffness Index□
Subject height □subjects height□
ΔT □the delay time between two peaks in a pulse waveform;

In addition, a difference between heights of the two peaks S and R is used to estimate the reflection intensity of reflected blood transmitted back in the artery, namely RI calculated as the following formula:

$$RI = \frac{a}{b} \times 100\% \qquad (2)$$

RI □Reflection Index□
a □amplitude of the first peak R
b □amplitude of the second peak S The foregoing is the principle for detecting blood pressure and pulse. Because the sphygmomanometer has no pulse analysis function, the invention provides an apparatus and method of detecting blood pressure and pulse, not only providing complete evaluation of the health of the cardiovascular system but also monitoring of health away from the clinical environment, e.g., at home. The embodiment is described as follows.

Figure 4:
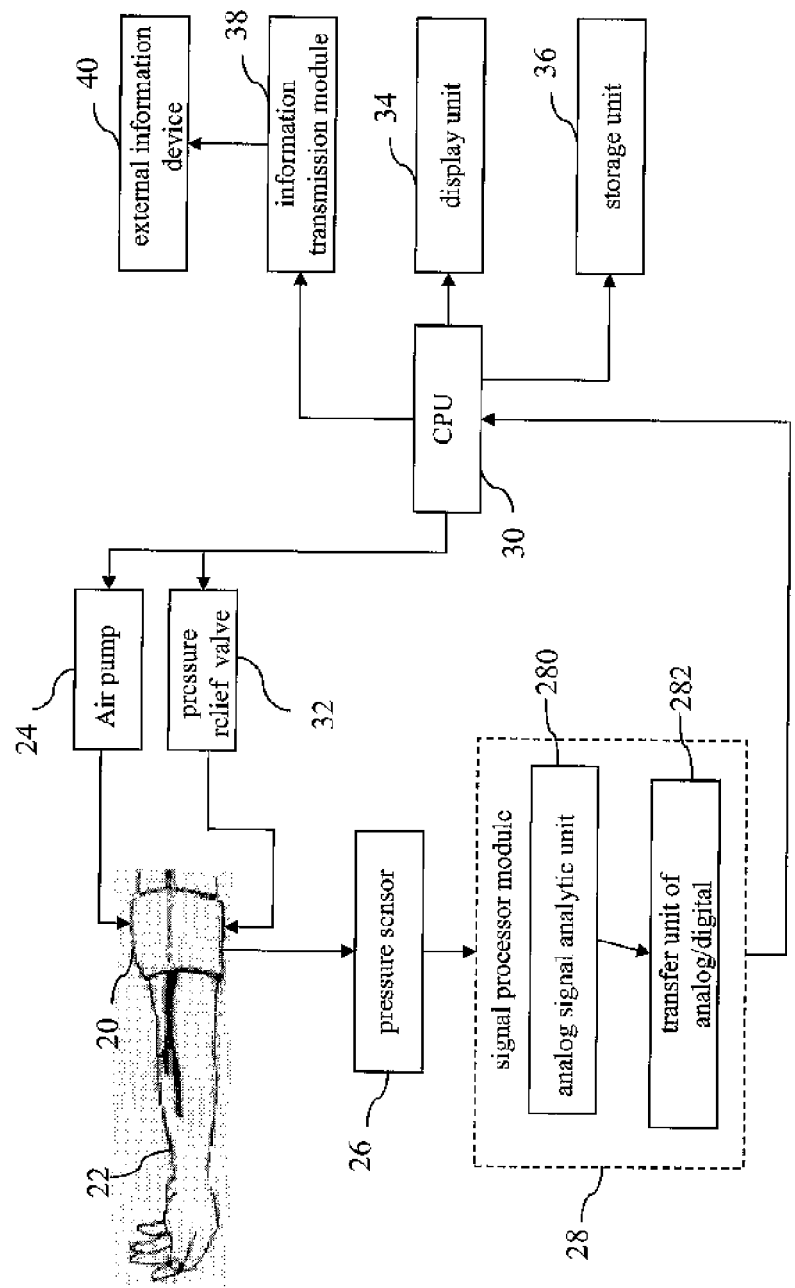
FIG. 4 is a block schematic diagram of an apparatus according to the present invention.

FIG. 4 is a block diagram of the invention. An inflatable cuff 20 is wrapped to any body part, such as brachium 22, wrist, or finger. An air pump 24 is connected to the inflatable cuff 20. The inflatable cuff 20 is inflated by actuating the air pump 24, and the blood vessel 14 is gradually compressed until blood flow is blocked. A pressure sensor 26 connected to the inflatable cuff 20 detects pressure variation thereof. When the inflatable cuff 20 is pressurized by the air pump 24, a signal of pressure variation is detected by the pressure sensor 26. The signal of pressure variation includes increased pressure sustained by the inflatable cuff 20 and an oscillating pressure produced by the blood flow during the pressure process.

A signal processor module 28 processing the signals detected by the pressure sensor 26 includes an analog signal analytic unit 280 and a transfer unit 282 for analog/digital formats (means for converting). The analog signal analytic unit 280 is utilized for analyzing and separating signals converted to digital format by the transfer unit 282 to achieve a pressure signal and a resonance signal. The pressure and resonance signals are delivered to the CPU 30 for calculation. After receiving the signals, the CPU 30 calculates the subject's blood pressure parameters, such as systolic and diastolic pressure and mean arterial pressure. A pressure relief valve 32 connected to the inflatable cuff 20 is controlled by the CPU 30 in accordance with at least one of systolic, diastolic, or mean arterial pressure or at least one of the predetermined pressure. Thus, a unique sequential pressure control of reduction and regulation of pressure is executed on the inflatable cuff 20 by the pressure relief valve 32. The reduction pressure signal from the inflatable cuff 20 is acquired by the pressure sensor 26. The reduction pressure signal analysis and format transformation through signal processor module 28 is described as follows.

During unique sequential pressure control of reduction and regulation of pressure, the pressure variation signal (the reduction pressure signal) to the inflatable cuff 20 is acquired. Similarly, the signal is analyzed and separated by the signal processor module 28, and a regulation pressure signal and a pulse signal of a blood vessel 14 are acquired. Both signals are delivered to the CPU 30 to work out at least one pulse signal, and at least one pulse parameter, such as SI, RI, etc., is acquired accordingly. Then, the blood pressure parameters and the pulse parameters are transmitted to a display unit 34, such as liquid crystal display [LCD] or light emitting diode [LED] display. The apparatus of the present invention further includes a storage unit 36, such as RAM, ROM, EEPROM, Flash RAM, or others, to store the blood pressure parameters, pulse signals, and the pulse parameters processed in the CPU 30. Through an information transmission module 38, such as USB, Blue Tooth, far-infrared parameters, RS232, or other module interfaces, the signals and parameters stored in the storage unit 36 can be delivered to an external information device 40, such as a computer, PDA, cell phone, database server, or others, to provide information for health management.

Figure 5:
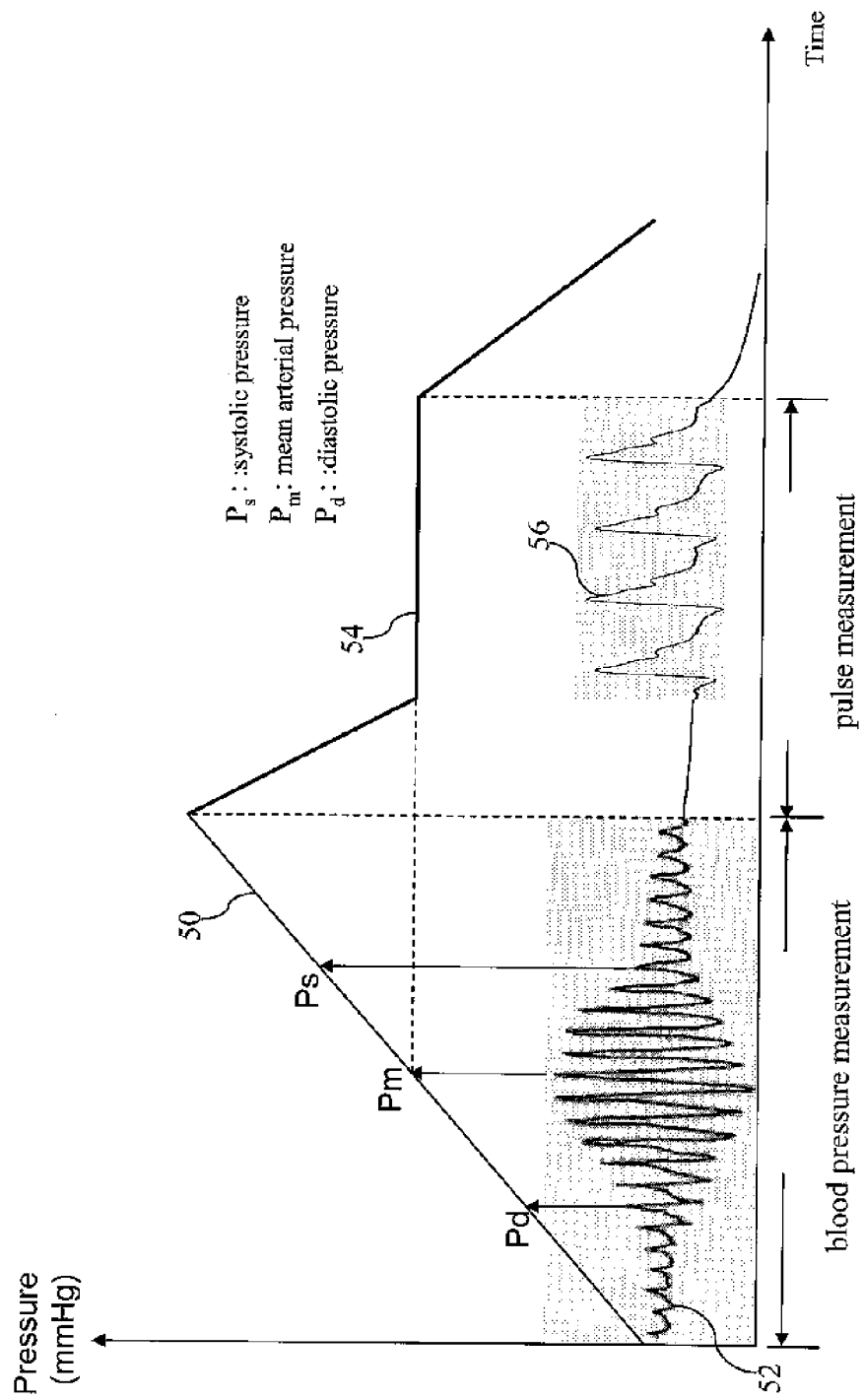
FIG. 5 is a schematic diagram of signal measurement based on the apparatus of the present invention.

FIG. 5 is a schematic diagram showing signal measurement as performed in the present invention. The measurement of the present invention includes a blood pressure measuring stage and a pulse measuring stage. First, in the blood pressure measuring stage, pressure in the inflatable cuff 20 is gradually increased until reaching a predetermined value, such as 180 mmHg, and the signal of pressure variation in the inflatable cuff 20 is acquired by the pressure sensor 26. After separating signals through the analog signal analytic unit 280, the pressure signal 50 and the resonance signal 52 in analog form are presented. After analog/digital conversion by the transfer unit 282, each amplitude of the resonant signal 52 is calculated by the CPU 30 to determine a maximum value. Compared with the pressure signal 50, the pressure of the maximum amplitude is set as the mean arterial pressure Pm. Maximum amplitude is respectively multiplied by 0.5, 0.8, etc., and the value is adjusted in accordance with the characteristic of elements and clinical results to determine the amplitude and position of the systolic pressure Ps and diastolic pressure Pd. After comparing the pressure signal 50, the systolic pressure Ps and the diastolic pressure Pd are acquired. Next, in the pulse measuring stage, the unique sequential pressure control of reduction and regulation of pressure is executed on the inflatable cuff 20 in accordance with at least one of systolic pressures Ps, mean arterial pressure Pm, diastolic pressure Pd or predetermined pressures value. In this embodiment, the mean arterial pressure Pm is employed. The CPU 30 controls the pressure relief valve 32 to maintain the pressure inside the inflatable cuff 20 at the mean arterial pressure for a predetermined time, such as 3 to 5 seconds, to allow registration of at least one complete pulse signal. Pressure variation in the inflatable cuff 20 (the reduction pressure signal) is detected by the pressure sensor 26. After the signal is processed by the signal processor module 28, the regulation signal 54 and the pulse signal 56 are separated and acquired as shown in FIG. 5. After analog/digital conversion, processing, and averaging by CPU 30, a single pulse of mean arterial pressure is acquired and provided for RI, SI calculation according to formulae (1) and (2).

Figure 6:
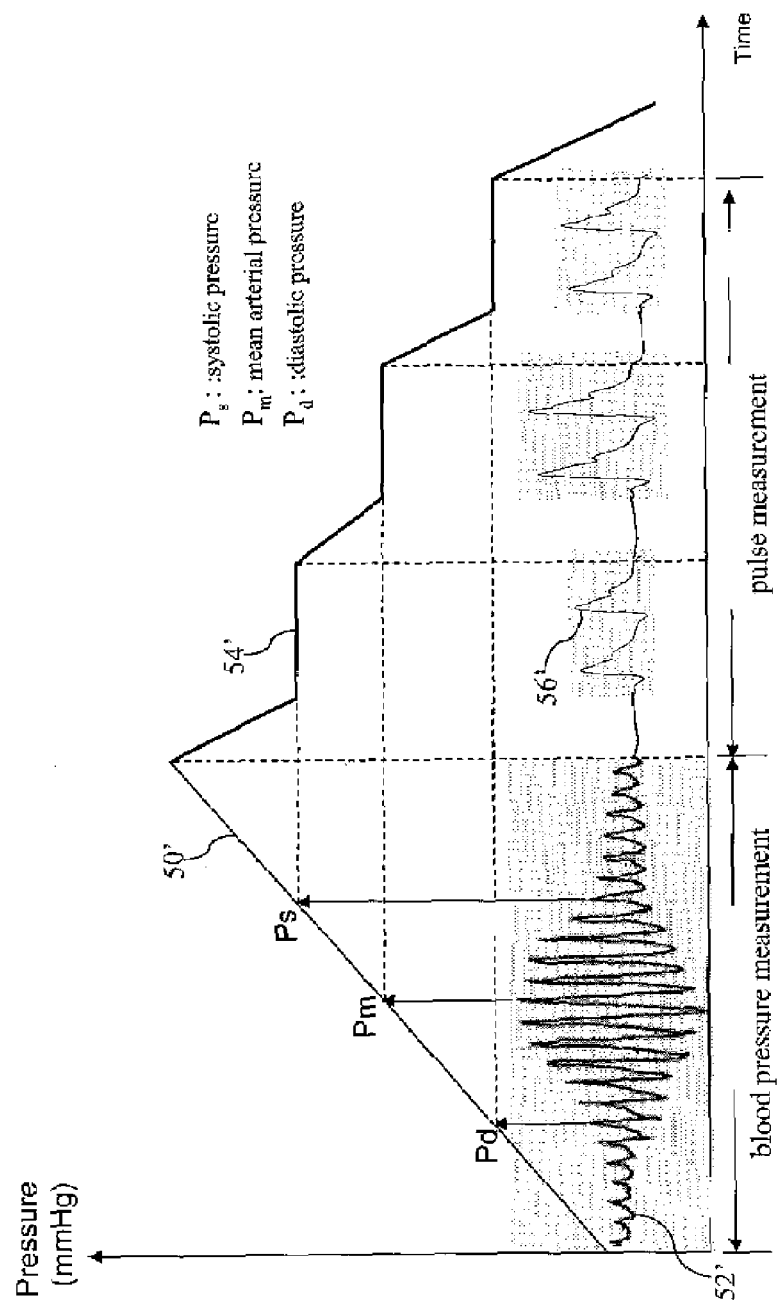
FIG. 6 is another schematic diagram of signal measurement based on the apparatus of the present invention.

FIG. 6 is another diagram showing a signal measurement of the present invention. The unique sequential pressure control of reduction and regulation of pressure is executed. The pressure of the inflatable cuff 20 is, respectively, maintained at the systolic pressure, the mean arterial pressure, and the diastolic pressure for a predetermined period. Similarly, the predetermined time is sufficient to record at least one complete pulse signal 56'. Pressure variation in the inflatable cuff 20 is detected (recorded) by the pressure sensor 26. Signal processor module 28 is employed to acquire a regulation pressure signal 54' and a pulse signal 56' as shown in FIG. 6. After analog/digital conversion, signals are sequentially processed through the CPU 30 in accordance with various pressures, such as systolic pressure, mean arterial pressure, and diastolic pressure, to acquire relative pulses under different pressures. The signals are, respectively, averaged to acquire a single pulse waveform for calculating blood parameters. The waveform under different pressures is further provided for Chinese Medical pulse diagnosis analysis. During the unique sequential pressure control of reduction and regulation of pressure, the blood pressure parameter as FIG. 6 shows is used to define pressure adjustment of inflatable cuff 20. The apparatus of the invention also can adjust pressure of the inflatable cuff 20 according to at least one predetermined pressure, such as 80 mmHg or 90 mmHg, or a plurality of predetermined values, such as 120 mmHg, 100 mmHg or 80 mmHg, are also capable. Thus, the pulse signal under single or various pressures is acquired.

The unique sequential pressure control of reduction and regulation of pressure of the present invention records pulse signals for calculation of blood vessel parameters. Different pulse signal under different pressures is further used for Chinese Medical pulse diagnosis analysis, in which a physician presses a blood vessel 14 deeply with fingers such that blood flow is nearly obstructed, a method referred to as "deep acquisition". Pressure is released until almost no pressure remains. This method is referred to as "drift acquisition". Finally, the physician presses between the "deep acquisition" and the "drift acquisition" to sense the characteristic of the pulse. This method is referred as to "middle acquisition". Based on the present invention, systolic pressure, diastolic pressure, and mean arterial pressure or predetermined plurality of pressure values provide a basis of pressure for the Chinese Medical pulse diagnosis theory. Working with an established database, known symptoms and corresponding results of "deep acquisition", "drift acquisition", and "middle acquisition" can improve Chinese Medical pulse diagnosis research.

While the invention has been explained in relation to preferred embodiment, it is to be understood that many other possible modifications and variations can be made without departing from the spirit and scope of the invention as hereinafter claimed.

What is claimed is:

1. An apparatus for pulse detection, based on blood pressure measuring stage, comprising:
   an inflatable cuff connected to a pressure sensor and applied to a subject's body part;
   an air pump connected to the inflatable cuff and providing an applied pressure of the inflatable cuff via an inflation, wherein the pressure sensor detects a signal of pressure variation in response to the applied pressure;
   a signal processor module electrically connected to the pressure sensor, receiving the signal of pressure variation and subsequent analyzing the signal of pressure variation to acquire a pressure signal and a resonance signal;
   a CPU electrically connected to the signal processor module, receiving the pressure signal and the resonance signal and calculating a blood pressure parameter of the subject;
   a pressure relief valve connected to the inflatable cuff for reducing the pressure therein in accordance with a predetermined pressure, wherein a unique sequential pressure control of reduction and regulation of pressure is executed on the inflatable cuff, a reduction pressure signal is detected by the pressure sensor, the reduction pressure signal is analyzed by the signal processor module, the analyzed reduction pressure signal is delivered to the CPU to acquire at least one pulse signal and at least one pulse parameter of the subject; and a display unit connected to the CPU displaying the blood pressure parameters and the pulse parameters, wherein the pulse parameter comprises at least one of a vascular stiffness index and a vascular reflection intensity.

2. The apparatus as claimed in claim 1, wherein the inflatable cuff is adapted to be wrapped to an arm, a wrist, or a finger of the subject.

3. The apparatus as claimed in claim 1, wherein the signal processor module comprises:

an analog signal analytic unit separating signals detected by the pressure sensor in accordance with the pressure applied to the inflatable cuff and the pressure reflected by a blood vessel of the subject; and a transfer unit to convert the separated signals to digital form.

4. The apparatus as claimed in claim 1, wherein the pressure applied to the inflatable cuff increases to at least 140 mmHg during the inflation.

5. The apparatus as claimed in claim 1, wherein the blood pressure parameter comprise at least one of a systolic pressure, a mean arterial pressure, and a diastolic pressure.

6. The apparatus as claimed in claim 1, wherein the predetermined pressure is set in accordance with the blood pressure parameter.

7. The apparatus as claimed in claim 1, wherein the CPU is further connected to a storage unit storing the blood pressure parameter, the pulse signal, and pulse parameter acquired.

8. The apparatus as claimed in claim 7, wherein the storage unit is a ROM, a RAM, a Flash RAM or an EEPROM.

9. The apparatus as claimed in claim 7, wherein the CPU is further connected to an information transmission module delivering the blood pressure parameter, the pulse signal, and pulse parameter stored in the storage unit to an external information device.

10. The apparatus as claimed in claim 9, wherein the information transmission module is a USB transmission interface, a RS232 transmission interface, a Blue Tooth transmission interface, a far-infrared transmission interface, or a modem.

11. The apparatus as claimed in claim 9, wherein the external information device is a computer, a digital personal assistant, a cell phone, or a database server.

12. A method for pulse detection, based on blood pressure measuring stage, comprising:

inflating an inflatable cuff wrapped to a subject, providing an applied pressure on the inflatable cuff;

recording a signal of pressure variation in response to the applied pressure;

separating the signal of pressure variation into a pressure signal and a resonance signal;

calculating a blood pressure parameter in accordance with the pressure signal and the resonance signal to acquire at least one blood pressure parameter of the subject;

executing a unique sequential pressure control of reduction and regulation of pressure on the inflatable cuff in accordance with at least one predetermined pressure;

recording a reduction pressure signal of the inflatable cuff during the unique sequential pressure control of reduction and regulation of pressure;

separating the reduction pressure signal to acquire a regulation pressure signal and a pulse signal;

calculating the regulation pressure signal and the pulse signal to acquire at least one pulse parameter of the subject; and outputting the blood pressure parameter and the pulse parameter, wherein the pulse parameter comprises at least one of a vascular stiffness index and a vascular reflection intensity.

13. The method as claimed in claim 12, the inflatable cuff is wrapped to an arm, a wrist, or a finger of the subject.

14. The method as claimed in claim 12, wherein the pressure applied to the inflatable cuff increases to at least 140 mmHg.

15. The method as claimed in claim 12, wherein the blood pressure parameter comprises at least one of a systolic pressure, a mean arterial pressure, and a diastolic pressure.

16. The method as claimed in claim 12, wherein a predetermined pressure value is set in accordance with the blood pressure parameter.

* * * * *